United States Patent [19]
Fuller

[11] Patent Number: 5,282,572
[45] Date of Patent: Feb. 1, 1994

[54] FRAGRANCE EMITTING ARTIFICIAL FLOWER-TYPE ARTICLE

[76] Inventor: Edward A. Fuller, 3100 Erie Dr., Orchard Lake, Mich. 48326

[21] Appl. No.: 926,282

[22] Filed: Aug. 10, 1992

[51] Int. Cl.⁵ .............................................. A61L 9/04
[52] U.S. Cl. ...................................................... 239/56
[58] Field of Search .................................. 239/54-60, 239/41, 53, 311

[56]  References Cited
U.S. PATENT DOCUMENTS

| | | | |
|---|---|---|---|
| 367,976 | 8/1887 | Hartmann | 239/55 |
| 593,329 | 11/1897 | McLaughlin | 239/55 |
| 3,120,345 | 2/1964 | Bolger | 239/60 X |
| 4,130,245 | 12/1978 | Bryson | 239/56 X |
| 4,161,284 | 7/1979 | Rattan | 239/56 X |
| 4,345,716 | 8/1982 | Armstrong et al. | 239/56 |
| 4,544,592 | 10/1985 | Spector | 239/56 X |
| 4,605,165 | 8/1986 | Van Loveren et al. | 239/56 X |

FOREIGN PATENT DOCUMENTS
292115  4/1915  Fed. Rep. of Germany .

*Primary Examiner*—Andres Kashnikow
*Assistant Examiner*—Kevin P. Weldon
*Attorney, Agent, or Firm*—Harness, Dickey & Pierce

[57] ABSTRACT

A long lasting, fragrance emitting, artificial flower display includes a number of artificial flowers and at least one flower-like stem upon which a number of bud or berry-like artificial formations are secured. Each formation is formed of a manually breakable capsule which is wrapped within an absorbent paper-type wrapper. The capsule contains a scent emitting, liquid substance which is released when the capsule is manually broken by squeezing the formation. The capsules may be broken, one by one, by successively squeezing them when desired to release the scent emitting substance for absorption by its respective wrapping so that the substance may evaporate and emit its scent into the surrounding area.

5 Claims, 1 Drawing Sheet

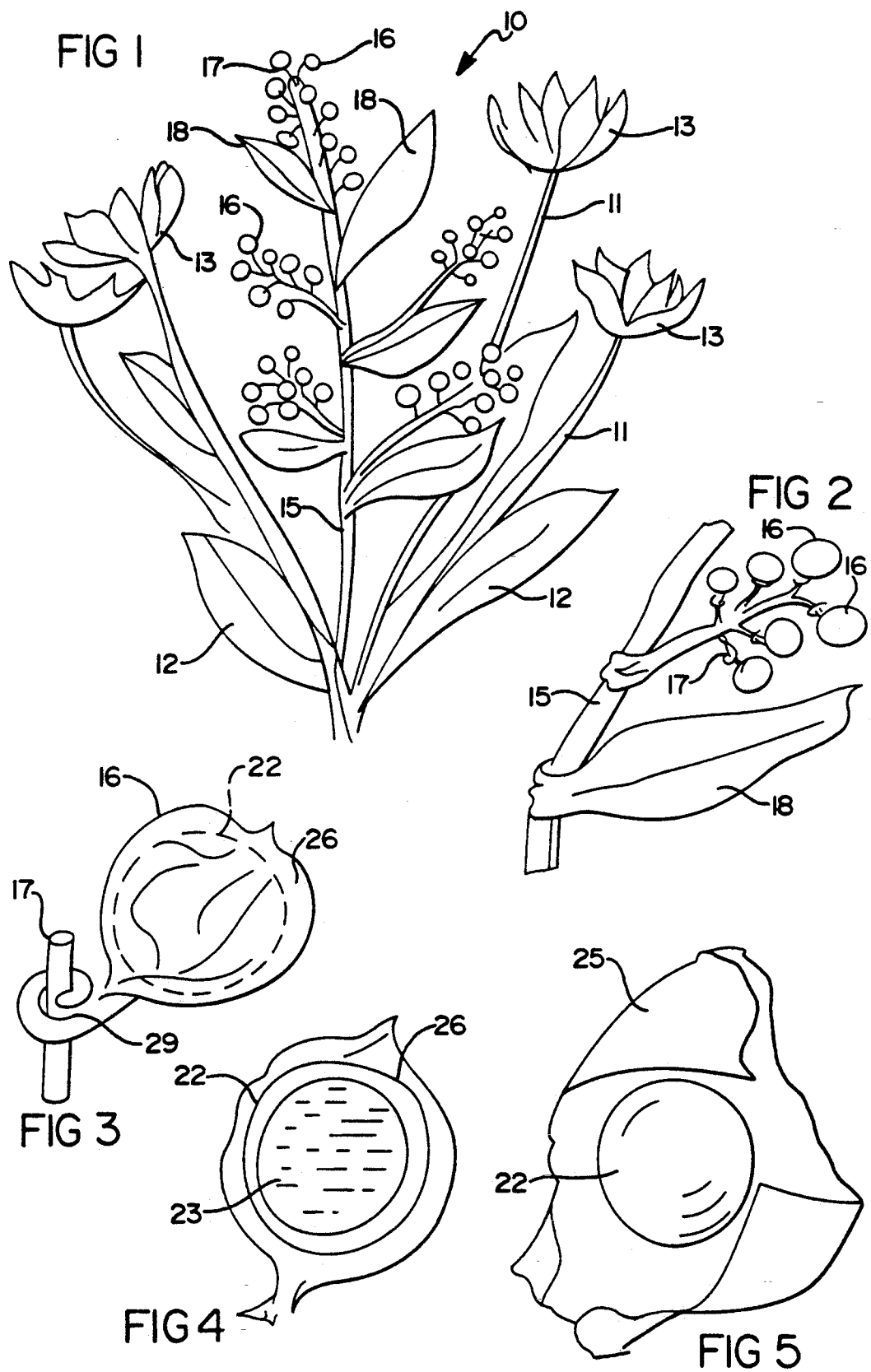

FRAGRANCE EMITTING ARTIFICIAL FLOWER-TYPE ARTICLE

BACKGROUND OF THE INVENTION

This invention relates to an artificial, flower-like article which stores scent emitting substances that may be released, when desired, to provide a fragrance in the vicinity of the article.

Artificial flowers normally comprise plastic or paper material formed into the shape of a floral type stem upon which are attached leaves, buds, berries, flower petals and the like. Conventionally, a number of generally similar artificial flowers are held together in a bunch to present a floral display.

In the past, attempts have been made to provide artificial flowers with a means for emitting a fragrance, such as a flower-like fragrance or other types of desirable fragrances. Thus, various types of containers having fragrance producing substances have been associated with artificial flowers. One example is a gelatin-type capsule or bubble within which a liquid, scent emitting substance is packaged so that upon release of the substance, a scent or fragrance is emitted. Such an example is disclosed in U.S. Pat. No. 3,556,916 issued to Levy on Jan. 19, 1971 for an "Artificial Flower including A Pieceable Casing Containing a Scent-Producing Substance". In this disclosure, a scent producing substance is contained within a ball shaped, gelatine casing having a thin wall which may be pierced to release the substance. The ball is intended to be mounted within a cup-like socket formed within the central portion of an artificial flower.

Examples of other prior flower-like, scent emitting articles are illustrated and disclosed in U.S. Pat. No. 1,720,881 to Brewster issued Jul. 16, 1929, U.S. Pat. No. 3,400,890 to Gould issued Jul. 10, 1968, U.S. Pat. No. 2,141,402 to Muller issued Dec. 27, 1938, U.S. Pat. No. 2,507,899 to Gilowitz issued May 16, 1950; U.S. Pat. No. 3,861,991 to Kim issued Jan. 21, 1975; U.S. Pat. No. 4,708,851 to Von Loringhoven issued Nov. 24, 1987 and U.S. Pat. No. 4,919,981 to Levy issued Apr. 24, 1990. An example of a plant-like article, in the form of a pine cone, containing a scent emitting substance is disclosed in U.S. Pat. No. 3,698,991 to Susewitz issued Oct. 17, 1972.

In the prior types of scent emitting flower-type articles, the scent emitting and containing portion of the article either was made for a relatively short time, single use, or are refillable for longer uses. That is, the single use type once operated to release the scent is no longer useful thereafter. The refillable type may have a scent material constantly fed to a scent emitting means. The scent material can be periodically refilled. Where the scent emitting means is a single use type, the floral display containing such scent emitting means has a limited life with respect to producing a fragrance. On the other hand, where the scent emitting means includes refilling a liquid or solid scent producing substance, attention must be given to the device from time to time to refill the container holding the substance.

Thus, it would be desirable to have a floral-type display article which can be used over a long period of time to provide a scent or fragrance whenever desired and for as long as desired within a pre-determined long time limit. The invention herein relates to a floral type of article, in the form of artificial buds or berries or the like which can be manually activated and can be selectively used over a considerable period of time to provide a desirable fragrance when desired either for a short period of time or for a longer period of time.

SUMMARY OF THE INVENTION

This invention relates to an artificial flower-type article formed of a stem, which may have leaves or flowers or the like attached thereto, with a substantial number of flower-type formations in the form of berries or buds or the like. The overall article is made to simulate a single flower-like or plant-like article. The formations are made of small containers or capsules, which may be formed of gelatin or a similar breakable and crushable material, within which a scent producing liquid substance is sealed. Each capsule or container is wrapped, preferably completely enclosed, within a paper-like, liquid absorbent, material which gives it the visual appearance of a bud or berry or similar plant formation. The formations may be broken by squeezing them with sufficient finger pressure to puncture the capsules and release the liquid substance which flows into and is absorbed by the surrounding wrapper. The substance evaporates from the wrapper to provide a fragrance in the vicinity of the article. The user of the article may release a fragrance from one formation at a time. This determines the length of time that the scent will be emitted, that is, until the amount of time it takes for the scent producing substance from that broken formation to completely evaporated. Then, the user may crush or break another formation to continue the scent emulsion. By successively squeezing the formations, one by one, the user may continue the emission of a fragrance for as long or as short a period as desired.

A substantial number of bud-like or berry-like or similar formations are attached upon a single flower-like stem so that the stem may be arranged within a bunch of otherwise conventional artificial flowers containing stems, leaves and flower petals and the like. Hence, the entire bunch may simulate an attractive floral display which will emit a desirable fragrance whenever desired and only for so long as desired. When the formations on the stem are all used, another such stem may be inserted in the bunch.

An object of this invention is to provide a simple, inexpensive means for producing a desirable scent or fragrance from an artificial floral display using a single article arranged within the display, which article contains a substantial number of hand breakable scent containing containers which, when broken, release a fragrance producing liquid substance. The substance is absorbed within a wrapper that surrounds each container for evaporation and scent emission. The wrapped containers visually simulate buds or berries. After the fragrance producing article is fully used up, it may be replaced without the necessity of replacing the entire floral bunch.

Another object of this invention is to provide an inexpensive article for use with a bunch of artificial flowers to produce a desirable scent or fragrance when desired and for as long as desired.

Yet another object of this invention is to provide a simple means for producing a fragrance emitting artificial flower-type article utilizing inexpensive and readily available materials without any substantial increase in the labor in making the article.

These and other objects and advantages of this invention will become apparent upon reading the following description of which the attached drawing forms a part.

BRIEF DESCRIPTION OF THE DRAWINGS

FIG. 1 schematically illustrates a bunch of artificial flowers with an artificial fragrance dispensing flower-like article included within the bunch.

FIG. 2 is an enlarged, schematic drawing showing a portion of the fragrance emitting article, namely, a collection of berry-like formations secured to an artificial stem.

FIG. 3 is a substantially enlarged berry-like formation schematically shown as attached to a portion of its stem.

FIG. 4 is a schematic, cross-sectional view of the berry-like formation of FIG. 3.

FIG. 5 is an enlarged, schematic view showing a scent producing manually breakable capsule arranged upon and ready to be wrapped within a paper-like wrapper to visually form a berry formation.

DETAILED DESCRIPTION

FIG. 1 schematically illustrates a bunch of artificial flowers 10. The artificial flowers are conventional. The construction of the flowers may vary and, therefore, forms no part of the invention herein. In general, each flower comprises a stem 11, leaves 12 and flowers 13. These items may be formed of plastic material, paper materials or other types of conventional sheet materials that are used in the construction of artificial flowers.

Contained within the bunch is an artificial stem 15 of a fragrance dispensing article. A substantial number of plant-like formations 16, such as formations that visually look like buds or berries 16, are mounted upon the stem by means of small attachment stems 17. In addition, artificial leaves 18 may be secured to the stem.

The plant-like formations, as illustrated in FIGS. 3–5, comprise a manually breakable or crushable container 22 which may be in the form of a gelatin capsule. The container or capsule contains a suitable, conventional, liquid scent emitting substance 23 (see FIG. 4). The particular scent emitting substance and the construction of the container or capsule may vary from among those commercially available and, therefore, the particular construction is not part of this invention. Those skilled in the art would be able to select a suitable capsule or container and scent emitting substance, such as that indicated, for example, in the above-mentioned U.S. Pat. No. 3,556,916.

The container or capsule 22 is surrounded by a paper-like sheet 25 which is wrapped around the container to form a wrapper 26. The paper is selected from a material which is able to absorb the liquid substance when it is released from its container so as permit the substance to evaporate into the surrounding area over a period of time. In addition, the paper may be wrapped around the capsule or container in such a way as to provide a small stem-like tail 29 (see FIG. 3) which may be secured to a small stem 17 or the main stem 15 as described above.

By selecting paper material which has an appropriate texture and color, the wrapped formation may appear visually to be a flower bud or a berry or a like formation which are naturally found upon flowers or plant-like materials.

In operation, the user assembles the fragrance dispensing article with a bunch of artificial flowers, such as within a holder or vase. Visually, the bunch simulates natural flowers. When it is desired to provide a fragrance in the area of the bunch, the user may squeeze, between the thumb and forefinger, one of the berry-like or bud-like formations to crush its capsule so as to release the scent emitting substance therefrom. The substance wets the paper wrapper and is absorbed into the paper from which it is evaporated into the surrounding area. The scent or fragrence released from the substance continues until the wrapper containing material is fully evaporated. Thus, the length of time for producing a fragrance from a single formation can be generally determined in advance and the user can plan accordingly in producing a fragrance.

Where it is desired to produce a fragrance over a longer period of time, the user need merely squeeze another formation and begin the evaporation process again. That can continue for as long as desired. Alternatively, the user may squeeze and release the scent emitting substance for relatively short periods of time by simply breaking only one capsule. Hence, the bunch of flowers with the fragrance emitting article may be used for a relatively long period of time without any attention other than periodically squeezing one or another of the formations whenever a fragrance is desired.

The user of the article may assemble more than one article within a bunch of flowers or a floral display in order to extend the life of that particular display. Alternatively, a single article may be provided. Whenever the scent emitting article is no longer effective, by reason of its release of the fragrance emitting material from each of its formations, another article may be substituted without loss of the remaining flowers within a particular floral display. Thus, an inexpensive, easily replaceable and easily operable means is provided for producing a scent when desired for as long as desired within either a new or a pre-existing floral display.

This invention may be further developed within the scope of the following claims. Accordingly, it is desired that the foregoing description as merely describing an operative embodiment of this invention and not in a strictly limiting sense.

Having fully described an operative embodiment of this invention, I now claim:

1. An artificial fragrance emitting flower article comprising:
    a flower stem having an artificial plant-type formation secured thereon;
    said formation including a plurality of sealed, but breakable under manual pressure, capsules containing a scent producing substance;
    with said capsules being wrapped within a liquid absorbing, paper wrapper which visually simulates a flower formation such as a bud or berry, and with the wrapper being made of a material which is wettable by, and which will absorb, the scent producing substance released from the capsule;
    said capsules being manually breakable by a hand applied squeezing pressure so that its scent producing substance is released from the capsules to wet and to be absorbed by the wrapper material and, thereafter, evaporate from the wrapper to emit a fragrance into the surrounding area and whereby the capsules contained therein may be manually broken, one by one, at different times when desired by a user to produce a desired fragrance in the area of the article at said different times.

2. An article as defined in claim 1 and including said wrapper completely encasing the capsule so as to enclose and absorb all the scent producing substance released from the capsule when the capsule is broken.

3. An article as defined in claim 1 and including said stem being arranged as part of a number of artificial flowers in a common holder to form a floral display of artificial flowers, which are decorative in appearance and emit a fragrance when desired by the selective breaking of the formation capsules one by one.

4. An artificial, fragrance dispensing flower article comprising:

an artificial stem such as is used for artificial flowers, with the stem having a plurality of artificial plant-type formations such as berries or buds and the like, secured thereto at spaced apart locations thereon;

each of said formations including at least one sealed, but manually breakable container which contains a scent producing, liquid substance;

each of said containers being wrapped within a paper wrapping material to visually simulate a flower formulation, and with the wrapping material being formed of a wettable, liquid absorbing, paper sheet wrapped around and enclosing said container;

said container being manually breakable by finger pressure squeezing so that its scent producing liquid substance may be released from the container and will wet the wrapping material and thereafter evaporate from the wrapping material into the surrounding area to emit a fragrance;

said wrapping material substantially completely encasing the container so as to absorb the scent producing liquid substance from the container when the container is broken;

and said article including a number of similar above-described formations, each secured to the stem in spaced apart relationship to the other formations secured thereon, whereby the containers of each formation may be manually broken, by finger squeezing, one by one, at different times when desired by a user in order to produce a desired fragrance at said different times.

5. An article as defined in claim 4 and including said stem being arranged with a number of artificial flowers together to form a floral display bunch of artificial flowers which present a visual floral display and, when desired, emit a fragrance by the breaking of selected containers.

* * * * *